United States Patent [19]

Lezdey et al.

[11] Patent Number: 5,093,316
[45] Date of Patent: Mar. 3, 1992

[54] TREATMENT OF INFLAMMATION

[76] Inventors: John Lezdey, 976 Kingston Dr., Cherry Hill, N.J. 08034; Allan Wachter, 9822 S. Grandview, Tempe, Ariz. 85284

[21] Appl. No.: 591,757

[22] Filed: Oct. 2, 1990

Related U.S. Application Data

[63] Continuation-in-part of Ser. No. 445,005, Dec. 4, 1989, Pat. No. 5,008,242, which is a continuation-in-part of Ser. No. 181,707, Apr. 14, 1989, abandoned, and a continuation-in-part of Ser. No. 242,735, Sep. 9, 1988, abandoned, which is a continuation-in-part of Ser. No. 948,445, Dec. 24, 1986, abandoned.

[51] Int. Cl.$^5$ ............................................. A61K 37/64
[52] U.S. Cl. ........................................ 514/8; 514/12; 514/21; 530/397
[58] Field of Search ................................ 514/8, 12, 21

[56] References Cited

U.S. PATENT DOCUMENTS

| | | | |
|---|---|---|---|
| 4,734,279 | 3/1988 | Stephan et al. | 424/85.8 |
| 4,916,117 | 4/1990 | Lezdey et al. | 514/8 |
| 5,008,242 | 4/1991 | Lezdey et al. | 514/8 |

OTHER PUBLICATIONS

Hubbard et al., Biochemical Efficacy and Safety of Monthly Augmentation Therapy for Alpha 1-Antitrypsin Deficiency-Sep. 2, 1988-vol. 260, No. 9.

Pannuculitis Associated with Severe 1-Antitrypsin Deficiency-Med. Affairs Arch Dermatol, vol. 123, Dec. 1987, Kevin C. Smith et al., Sequence Homology Between Human.

1-Antichymotrypsin 1-Antitrypsin and Antitrambin III-Amer. Chem. Soc., vol. 22-No. 22, 1983-T. Chandra et al.

Cloning, Expression, Purification, and Biological Acitivty of Recombinant Native and Variant Human 1-Antichymotrypsins, J. of Bio. Chem., vol. 265, No. 2, Jan. 15, pp. 1199-1207, 1990, Rubin et al.

Structure, Function, and Control of Neutrophil Proteinases, The American Journal of Medicine, vol. 84, Travis et al.

J. Amer. Acad. of Dermatology, "The Mast Cell in Health & Disease", Rothe et al., vol. 23, No. 4, Part 1, pp. 615-624, Oct. 1990.

Allergy Proc., "The Mast Cell: A Comprehensive Update Review", Bernstein et al., Sep.-Oct. 1990, vol. 11, No. 5, pp. 209-223.

Dr. Ishizaka, M.D., Ph. D., Scientific Director, La Jolla Institute for Allergy and Immunology, Letter of Sep. 1991.

Respiratory News, p. 5, Mar. 1991.

The J. of Allergy and Clinical Immunology, vol. 87, No. 5, pp. 893-910, Kay, May 1991.

Air Engineering Systems Corp., Multi-Processing System, pp. 1-18.

Brochure 213/3e, Air Engineering Systems Corp.

Micron Powder Systems, pp. 1-12, 1990.

In Allergy, vol. No. 1, Apr. 1990, Ernest N. Charlesworth, pp. 1-4.

*Primary Examiner*—Howard E. Schain
*Attorney, Agent, or Firm*—John Lezdey

[57] ABSTRACT

A method for treating pulmonary inflammation and alpha-l-antitrypsin deficiencies by the administration of an effective amount of microcrystalline alpha-1-antitrypsin, its salt or derivative by inhalation, alone or with other serine protease inhibitors, and the pharmaceutical compositions thereof.

8 Claims, No Drawings

TREATMENT OF INFLAMMATION

RELATED APPLICATION

This application is a continuation-in-part of application Ser. No. 445,005 filed Dec. 4, 1989, now U.S. Pat. No. 5,008,242 which is a continuation-in-part of application Ser. No. 181,707 filed Apr. 14, 1989, now abandoned and Ser. No. 242,735, filed Sept. 9, 1988, now abandoned, which are continuations-in-part of application Ser. No. 948,445 filed Dec. 24, 1986, now abandoned.

FIELD OF THE INVENTION

The present invention relates to a method and composition for treating mammals afflicted with a certain inflammatory disease. More particularly, the present invention relates to the treatment of certain pulmonary diseases and/or symptoms of the disease in mammals by administering microcrystalline alpha-1-antitrypsin the salts or derivatives thereof alone or with other serine protease inhibitors by inhalation or nebulization.

BACKGROUND OF THE INVENTION

Alpha-1-proteinase inhibitor is a glycoprotein having a molecular weight of 53,000 determined by sedimentation equilibrium centrifugation. The glycoprotein consists of a single polypeptide chain to which several oligosaccharide units are covalently bonded. Human alpha-1-proteinase inhibitor has a role in controlling tissue destruction by endogenous serine proteinases. A genetic deficiency of alpha-1-proteinase inhibitor, which accounts for 90% of the trypsin inhibitory capacity in blood plasma, has been shown to be associated with the premature development of pulmonary emphysema. The degradation of elastin associated with emphysema probably results from a local imbalance of elastolytic enzymes and the naturally occurring tissue and plasma proteinase inhibitors. Alpha-1-proteinase inhibitor inhibits human pancreatic and leukocyte elastases. See Pannell et al, Biochemistry. 13, 5339 (1974); Johnson et al, Biochem. Biophys. Res. Commun., 72 33 (1976); Del Mar et al, Biochem. Biophys. Res. Commun., 88, 346 (1979); and Heimburger et al, Proc. Int. Res. Conf. Proteinase Initiators. 1st, 1-21 (1970).

U.S. Pat. No. 4,916,117 to Lezdey et al discloses the treatment of pulmonary inflammation with microcrystalline alpha-1-antichymotrypsin.

It is understood that the use of the terms "alpha-1-antichymotrypsin", "alpha-1-antitrypsin" and "C-reactive protein" is meant to include those serine protease inhibitors in the native as well as recombinant form.

SUMMARY OF THE INVENTION

The present invention relates to a method for treating inflammatory conditions of the pulmonary tract by the administration of alpha-1-antitrypsin, the salts or derivatives thereof in a suitable pharmaceutical composition for inhalation therapy.

Among the inflammatory conditions which may be treated with alpha-1-antitrypsin there are included inflammations of the tracheobronchial tree such as asthma, emphysema, chronic obstructive pulmonary disease and chronic granulomatous lung disease i.e. Sarcoid.

The use of alpha-1-antitrypsin is especially useful in the treatment of the various inflammatory lung conditions including those which are induced by smoking or generically deficient $\alpha$1-antitrypsin diseases.

The addition of other serine protease inhibitors such as alpha-1-antichymotrypsin and/or C-reactive protein provides a broader spectrum for treating associated symptoms of inflammation.

The drugs of the invention may be cloned by conventional techniques utilizing an antibody probe. For example, ar antibody against C1-esterase inhibitor or alpha-1-antichymotrypsin can utilized as the probe. It has been found that the $\alpha$1-antichymotrypsin inhibitor is not cross-reactive with any other native proteins in human serum as examined by immuno-diffusion assays. The recombinant gene product of the invention is especially useful since it is free of contaminating viruses when produced.

The salts and derivatives of the serine protease inhibitors may be formed utilizing conventional techniques associated with other proteins without effecting the utility of the compound. There may be prepared the alkali metal salts, acid-addition salts, and esters similar to other proteins or peptides.

It is the object of the invention to provide an anti-inflammatory composition which can be used as a prophylaxis and/or in treatment of existing inflammatory pulmonary diseases, particularly, emphysema.

It is another object of the invention to provide a composition for smokers which can prevent or treat irritations arising from tobacco use.

It is a further object of the invention to provide an anti-inflammatory composition for pulmonary diseases which is well tolerated by the human body and is free of side effects.

DETAILED DESCRIPTION OF THE PRESENT INVENTION

The object of the present invention can be achieved by the administration of microcrystalline alpha-1-antitrypsin in suitable pharmaceutical form to patients suffering from inflammatory conditions of the pulmonary tract by nebulization and other forms of inhalation therapy.

The present invention provides a pharmaceutical composition which comprises the alpha-1-antitrypsin in combination with other serine protease inhibitors such as alpha-1-antichymotrypsin and/or C-reactive protein.

Normally between 50 and 100 mcg of the compositions of the invention will be administered each day of treatment (to an average 70 kg adult). Similar amounts may be administered to prevent the occurrence of the condition.

In the treatment of chronic cases of inflammatory lung conditions wherein the cells express proteases, such as in the case of emphysema, the patient is typically administered intravenously 15 to 90 mg of alpha-1-antichymotrypsin compound per kilogram of body weight weekly at a rate of 2 mg per kilogram per minute. The treatment is continued for a period of time until there is a reversal of the biochemical abnormalities in serum and lung fluid that characterizes the disorder. The treatment may be followed up by administration of the drug by inhalation to more rapidly promote healing. For use in the prevention of the disease, the drug may be administered orally or by inhalation techniques on a weekly basis. This weekly treatment is believed to aid smokers from incurring the inflammation of the pulmonary tract which is commonly associated with smoking.

The active ingredient of the invention may be incorporated into a metered-dose aerosol unit containing a microcrystalline suspension of the drug in a mixture of halogenated hydrocarbon propellants alone or with a carrier such as oleic acid. Preferred propellants are trichloromonofluoromethane and dichlorodifluoromethane or mixtures thereof. Each unit has a molecular proportion of active ingredient to the halogenated hydrocarbon between 3:1 and 3:2. Each actuation of the aerosol cannister delivers a quantity of drug equivalent to 42-90 mcg.

The inhaler is useful for prophylactic use as well as for direct treatment of pulmonary diseases or inflammations.

Emphysema and alpha-1-antitrypsin deficiencies are currently being treated by injection or infusion of a composition containing alpha-1-antrypsin marketed by Miles Laboratories, Inc., under the trademark PROLASTIN. However, such form of administered does not provide the rapid relief of the symptom associated with the disease, particularly, inflammation.

Emphysema also results in the occurrence of the neutrophils cathepsin G and elastase which cause destruction of the tissues. Alpha-1-antitrypsin only controls elastase. It is therefore advisable to utilize other serine protease inhibitors such as alpha-1-antichymotrypsin to obtain a broader spectrum of therapy for use in treatment and control of the disease. The administration of the useful serine protease inhibitors directly to the site of the disease, such as by inhalation, has teen found to provide a rapid relief for the patient with a smaller drug requirement.

The following examples further illustrate the practice of this invention, but are not intended to be limiting thereof. It will be appreciated that the selection of actual amounts of specific alpha-1-antitrypsin or other serine protease inhibitors to be administered to any individual patient (human or animal) will fall within the discretion of the attending physician and will be prescribed in a manner commersurate with the appropriate dosages will depend on the patient's age, weight, sex, stage of disease and like factors uniquely within the purview of the attending physician.

EXAMPLE I

Microcrystalline alpha-1-antitrypsin is suspended in oleic acid and added into a metering aerosol cannister together with trichloromonofluoromethane and dichlorodifluoromethane so that the unit has a molecular proportion of alpha-1-antitrypsin to the propellant between 3:1 and 3:2. The unit delivers a quantity of drug equivalent to 42 mcg.

EXAMPLE II

Microcrystalline alpha-1-antichymotrypsin and alpha-1-antitrypsin is suspended in oleic acid and added into a metering aerosol cannister together with trichloromonofluoramethane and dichlorodifluoromethane so that the unit has a molecular proportion of drug to the propellant between 3:1 and 3:2.

If desired, microcrystalline C-reactive protein may be added in an equal amount to the drug to form a ratio of 1:1:1 of active ingredients.

We claim:

1. A method for treating the symptoms of pulmonary inflammation in pulmonary diseases which express proteases which comprises administering an effective amount of microcrystalline alpha-1-antitrypsin, the derivatives or salts thereof by inhalation whereby elastase and cathepsin G are controlled.

2. The method of claim 1 wherein said disease is emphysema.

3. The method of claim 1 administering in an effective amount of other serine protease inhibitors.

4. The method of claim 3 wherein said other serine protease inhibitors is selected from the group consisting of alpha-1-antichymotrypsin, C-reactive protein, and mixtures thereof.

5. The method of claim 1 wherein said disease is asthma.

6. A pharmaceutical composition for treating inflammatory pulmonary conditions in pulmonary diseases which express proteases which include elastase and cathepsin G by inhalation therapy comprising an effective amount of microcrystalline alpha-1-antitrypsin and an inert propellant.

7. The pharmaceutical composition of claim 6 including at least one other serine protease inhibitor.

8. The pharmaceutical composition of claim 7 wherein said other protease inhibitor is selected from the group consisting of alpha-1-antichymotrypsin, C-reactive protein and mixtures thereof.

* * * * *